(12) United States Patent
Xie et al.

(10) Patent No.: US 12,292,997 B2
(45) Date of Patent: May 6, 2025

(54) INTER-HOSPITAL ELECTRONIC MEDICAL RECORD ACCESS AUTHENTICATION PROTOCOL BASED ON BLOCKCHAINS

(71) Applicant: Hangzhou Normal University, Hangzhou (CN)

(72) Inventors: Qi Xie, Hangzhou (CN); Xiumei Li, Hangzhou (CN); Zixuan Ding, Hangzhou (CN); Bin Hu, Hangzhou (CN); Xiao Tan, Hangzhou (CN); Lidong Han, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 188 days.

(21) Appl. No.: 18/355,402

(22) Filed: Jul. 19, 2023

(65) Prior Publication Data

US 2024/0028761 A1 Jan. 25, 2024

(30) Foreign Application Priority Data

Jul. 22, 2022 (CN) .......................... 202210866277.7

(51) Int. Cl.
| | |
|---|---|
| G06F 21/62 | (2013.01) |
| G16H 10/60 | (2018.01) |
| G16H 40/20 | (2018.01) |
| H04L 9/00 | (2022.01) |
| H04L 9/08 | (2006.01) |
| H04L 9/32 | (2006.01) |

(52) U.S. Cl.
CPC ......... *G06F 21/6245* (2013.01); *G16H 10/60* (2018.01); *G16H 40/20* (2018.01); *H04L 9/0838* (2013.01); *H04L 9/3234* (2013.01); *H04L 9/3297* (2013.01); *H04L 9/50* (2022.05)

(58) Field of Classification Search
CPC .... G06F 21/6245; G16H 10/60; G16H 40/20; H04L 9/0838; H04L 9/3234; H04L 9/3297; H04L 9/50; H04L 9/0841; H04L 2209/88; H04L 9/14; H04L 9/3013; H04L 9/3066; H04L 63/0435; H04L 63/0457; H04L 67/12
See application file for complete search history.

(56) References Cited

U.S. PATENT DOCUMENTS

10,796,393 B2 * 10/2020 Messerges ........... G06Q 50/265
11,120,432 B2 * 9/2021 Kurian ............... G06Q 20/3821
(Continued)

*Primary Examiner* — Harunur Rashid (57) ABSTRACT

A method for inter-hospital identity authentication and electronic medical record transfer of patients is provided. Based on a blockchain technology, a patient achieves secure and efficient inter-hospital transfer authentication, and a new hospital accesses an electronic medical record with authorization of the patient, thus achieving reliable electronic medical record access controls. In each hospital, the patient, a medical server, and a doctor achieve efficient tripartite authentication and negotiation of session keys, and communicate based on the session keys. By introducing an elliptic curve to encrypt key parameters in an authentication process, a security of the entire authentication process is improved, and a computational pressure on a wireless device is reduced. In the authentication and the electronic medical record, the patient uses dynamic anonymity policies to protect privacy.

9 Claims, 7 Drawing Sheets

(56) References Cited

U.S. PATENT DOCUMENTS

| | | | |
|---|---|---|---|
| 2007/0143398 A1* | 6/2007 | Graham | G06Q 40/02 709/204 |
| 2019/0287199 A1* | 9/2019 | Messerges | H04L 51/18 |
| 2020/0084037 A1* | 3/2020 | Zhang | H04L 9/3226 |
| 2020/0119922 A1* | 4/2020 | Bingham | H04L 9/0637 |
| 2021/0273812 A1* | 9/2021 | Hardin | H04L 9/0894 |

* cited by examiner

INTER-HOSPITAL ELECTRONIC MEDICAL RECORD ACCESS AUTHENTICATION PROTOCOL BASED ON BLOCKCHAINS

TECHNICAL FIELD

The disclosure relates to a field of information security technologies, in particular to an inter-hospital electronic medical record access authentication protocol based on blockchains.

BACKGROUND

Intelligent healthcare provides convenient and personalized services for patients based on an advanced information technology and an internet of medical things (IoMT) technology. However, in practical applications, patients transfer authentication and electronic medical record access controls among different hospitals are still difficult and cumbersome. The patient usually needs to re-register and authenticate when transferring to another hospital, and a previous electronic medical record is difficult to share, forming an information island, which is a great waste of public resources.

Medical data mainly based on electronic medical records has always been under threats of attacks, and attackers use various attack methods to steal medical data of patients from a medical system. Centralization of the medical system increases risks of data breaches when attacked. Digitization and informatization of the medical systems is an inevitable trend of development, and ensuring an efficient identity transfer among hospitals and secure access controls of transferred electronic medical records is of great significance for the digitization of the medical system and a privacy protection of the patients.

Compared to other encryption algorithms, elliptic curve cryptosystems are particularly suitable for devices with limited computing and storage resources owning to their advantages such as short keys, high strength, fewer parameters, fast digital signatures, and small computational data. A blockchain technology has characteristics of a decentralization, non-tampering, and non-forgery, and using a blockchain for the storage and the access control of the electronic medical records can ensure a security of the electronic medical records.

SUMMARY

In order to solve problems existing in current medical scenes, the disclosure proposes an inter-hospital electronic medical record access authentication method based on a blockchain. The method is applicable to inter-hospital authentication and inter-hospital medical record access controls of patients in a medical system, and has characteristics of anti-attack, tamper resistance of medical records, dynamic anonymity of patient identities, a privacy protection, and an access control of inter-hospital medical records.

In order to achieve above purposes, the disclosure adopts a Diffie-Hellman key exchange (DHKE) and introduces elliptic curve cryptography to encrypt and protect key parameters in authentication processes, meanwhile, adds a three factor authentication method to resist offline password guessing attacks and session key disclosure attacks, thus improving a security of an entire authentication process. Simultaneously a blockchain technology is used to achieve a sharing of electronic medical records and authorized secure access controls.

An inter-hospital electronic medical record access authentication method based on a blockchain includes the following steps:

S1: a medical server is initialized;

S2: a patient and a doctor submit registration requests to the medical server through a user device of the patient and a device of the doctor, after the medical server verifies legality of identities of the patient and the doctor, registration messages are fed back to the user device of the patient and the device of the doctor, and the registration messages of the patient and the doctor are stored on a smart card of the patient and the device of the doctor respectively;

S3: the user device of the patient submits an initialize authentication request to the medical server;

S4: the doctor performs a diagnosis on the patient when the patient, the medical server, and the doctor complete initialize authentication and negotiate session keys for communications, and the medical server uploads an electronic medical record of the patient to the blockchain;

S5: the patient submits a transfer authentication request to a medical server of another hospital where the patient is located when the patient is transferred to the another hospital; and S6: in the another hospital, after the patient, a medical server, and a doctor complete transfer authentication, negotiate and verify session keys for communications, the patient authorizes the medical server to access the electronic medical record of the patient, and the doctor performs a diagnosis on the patient, the medical server uploads another electronic medical record of the patient to the blockchain.

In an embodiment, the medical server is initialized in the S1 as follows: the medical server selects an $E(GF_q)$ function of an elliptic curve and selects a base point P on the elliptic curve; then selects a server key $k_{MSj}$ and stores the server key $k_{MSj}$ secretly in the medical server, and the medical server calculates a public key $PK_{MSj}$ through the $E(GF_q)$ function of the elliptic curve, finally exposes parameters $\{E(GF_q), P, PK_{MSj}\}$.

In an embodiment, the S2 includes the steps as follows:

S2.1: the patient inputs an identity $ID_i$, a password $PW_i$ and biological message $bio_i$ into the user device; and the user device sends the identity $ID_i$ to the medical server through a secure channel;

S2.2: after receiving and verifying legality of the identity $ID_i$ of the patient, the medical server calculates a secret value $b_i$ between the patient and the medical server, and sends the registration message of the patient to the user device through a secure channel, and stores the registration message of the patient in the smart card;

S2.3: the doctor inputs an identity $DID_n$, a password $PW_n$, and biological message $bio_n$ into the device, and the device sends the identity $DID_n$ to the medical server through a secure channel; and S2.4: after receiving and verifying legality of the identity $DID_n$ of the doctor, the medical server calculates a secret value $b_n$ between the doctor and the medical server, and sends the registration message of the doctor to the device of the doctor through a secure channel, and store the registration message of the doctor in the device of the doctor.

In an embodiment, the initialize authentication in the S4 is based on bidirectional authentication and key negotiation and verification among the smart card and the user device of the patient, the medical server and the device of the doctor;

and uploading the electronic medical record of the patient in the S4 is based on a mutual confirmation among the smart card and the user device of the patient, the medical server and the device of the doctor, and the electronic medical record is uploaded to the blockchain by the medical server.

In an embodiment, steps of the initialize authentication, the key negotiation and verification, and uploading the electronic medical record of the patient are as following:

S4.1: the patient inserts the smart card into the user device, and after passing identity authentication, the user device generates a current timestamp $T_1$ through the registration message in the smart card, calculates verification parameters, and sends a message $MES_1^j$ to the medical server;

S4.2: after receiving the message $MES_1^j$, the medical server verifies legality of the timestamp $T_1$ and the validation parameters in the message $MES_1^j$; the bidirectional authentication is terminated when the timestamp $T_1$ and the validation parameters are not legal, or authentication from the smart card of the patient to the medical server is successful when the timestamp $T_1$ and the validation parameters are legal;

S4.3: after the authentication from the smart card of the patient to the medical server is successful, the medical server generates a temporary identity $TID_i$ of the patient and a current timestamp $T_2$, calculates verification parameters, and sends a message $MES_2^j$ to the device of the doctor;

S4.4: the device of the doctor receives the message $MES_2^j$ and verifies legality of the timestamp $T_2$ and the validation parameters in the message $MES_2^j$; the bidirectional authentication is terminated when the timestamp $T_2$ and the validation parameters are not legal, or authentication from the medical server to the device of the doctor is successful when the timestamp $T_2$ and the validation parameters are legal;

S4.5: after the authentication from the medical server to the device of the doctor is successful, the device of the doctor generates a current timestamp $T_3$, a session key $SK_{nj}$ used for communicating with the medical server and a session key $SK_{in}$ used for communicating with the patient, calculates validation parameters, and sends a message $MES_3^j$; to the medical server;

S4.6: after receiving the message $MES_3^j$, the medical server verifies legality of the timestamp $T_3$ and the validation parameters in the message $MES_3^j$; the bidirectional authentication is terminated when the timestamp $T_3$ and the validation parameters are not legal, or authentication from the device of the doctor to the medical server is successful when the timestamp $T_3$ and the validation parameters are legal;

S4.7: after the authentication from the device of the doctor to the medical server is successful, the medical server generates a current timestamp $T_4$, a session key $SK_{nj}'$ used for communicating with the device of the doctor and a session key $SK_{ij}$ used for communicating with the user device of the patient, calculates verification parameters, and sends a message $MES_4^j$ to the user device of the patient;

S4.8: after receiving the message $MES_4^j$, the user device of the patient verifies legality of the timestamp $T_4$ and the validation parameters in the message $MES_4^j$; the bidirectional authentication is terminated when the timestamp $T_4$ and the validation parameters are not legal, or the user device calculates and verifies a session key $SK_{in}'$ used for communicating with the doctor and a session key $SK_{ij}'$ used for communicating with the medical server when the timestamp $T_4$ and the validation parameters are legal; and the smart card and the user device of the patient, the medical server and the device of the doctor successfully negotiate the session keys with each other when the verification of the session key $SK_{in}$ and the session key $SK_{ij}$ is successful;

S4.9: after the patient and the doctor communicates with each other by using the session key $SK_{in}$, the doctor performs a diagnosis $Dia_n$ on the patient, the device of the doctor generates a current timestamp $T_6$, calculates verification parameters, and sends message $MES_5^j$ to the medical server;

S4.10: after receiving the message $MES_5^j$, the medical server verifies legality of the timestamp $T_6$ and the validation parameters in the message $MES_5^j$; the bidirectional authentication is terminated when the timestamp $T_6$ and the validation parameters are not legal, or a source of a diagnostic result is reliable and verification of the medical server is successful when the timestamp $T_6$ and the validation parameters are legal;

S4.11: after the medical server verifies legality of the diagnosis result, the medical server generates a current timestamp $T_7$ and the electronic medical record of the patient, calculates validation parameters, uploads the electronic medical record to the blockchain, and sends a message $MES_6^j$ to the user device of the patient; and S4.12: after receiving the message $MES_6^j$, the user device of the patient verifies legality of the timestamp $T_7$ and the validation parameters in the message $MES_6^j$; the bidirectional authentication is terminated when the timestamp $T_7$ and the validation parameters are not legal, or the electronic medical record is reliable and contents of the electronic medical record is held accountable when the timestamp $T_7$ and the validation parameters are legal.

In an embodiment, the transfer authentication in the S6 is based on bidirectional authentication and key negotiation and verification among the smart card and user device of the patient, the medical server and a device of the doctor, and uploading the new electronic medical record in the S6 is based on mutual confirmation among the smart card and user device of the patient, the medical server and a device of the doctor, and the new electronic medical record is uploaded to the blockchain by the medical server.

In an embodiment, steps of the transfer authentication, the key negotiation and verification, and uploading the electronic medical record are as follows:

S6.1: the patient inserts the smart card into the user device, and after passing identity authentication, the user device generates a current timestamp $T_8$ through the registration message in the smart card, calculates verification parameters, and sends a message $MES_1^x$ to the medical server;

S6.2: after receiving the message $MES_1^x$, the medical server verifies legality of the timestamp $T_8$ and the validation parameters in the message $MES_1^x$; the bidirectional authentication is terminated when the timestamp $T_8$ and the validation parameters are not legal, or authentication from the smart card of the patient to the medical server is successful when the timestamp $T_8$ and the validation parameters are legal;

S6.3: after the authentication from the smart card of the patient to the medical server is successful, the medical server generates a new temporary identity $TID_i$ for the patient, downloads the electronic medical record of the patient from the blockchain based on authorization of the electronic medical record of the patient, then generates a current timestamp $T_9$ and calculates verification parameters, and sends message $MES_2^x$ to the device of the doctor;

S6.4: the device of the doctor receives the message $MES_2^x$ and verifies legality of the timestamp $T_9$ and the validation parameters in the message $MES_2^x$; the bidirectional authentication is terminated when the timestamp $T_9$ and the validation parameters are not legal, or authentication from the medical server to the device of the doctor is successful when the timestamp $T_9$ and the validation parameters are legal;

S6.5: after the authentication from the medical server to the device of the doctor is successful, the device of the doctor generates a current timestamp $T_{10}$, a session key $SK_{tx}$ used for communicating with the medical server and a session key $SK_{it}$ used for communicating with the patient, calculates validation parameters, and sends a message $MES_3^x$ to the medical server;

S6.6: after receiving the message $MES_3^x$, the medical server verifies legality of the timestamp $T_{10}$ and the validation parameters in the message $MES_3^x$; the bidirectional authentication is terminated when the timestamp $T_{10}$ and the validation parameters are not legal, or authentication from the device of the doctor to the medical server is successful when the timestamp $T_{10}$ and the validation parameters are legal;

S6.7: after the authentication from the device of the doctor to the medical server is successful, the medical server generates a current timestamp $T_{11}$, the session key $SK_{tx}$, used for communicating with the doctor and a session key $SK_{ix}$, used for communicating with the patient, calculates verification parameters, and sends a message $MES_4^x$ to the user device of the patient;

S6.8: after receiving the message $MES_4^x$, the user device of the patient verifies legality of the timestamp $T_{11}$ and the validation parameters in the message $MES_4^x$; the bidirectional authentication is terminated when the timestamp $T_{11}$ and the validation parameters are not legal, or the user device calculates and verifies the session key $SK_{it}$ used for communicating with the doctor and the session key $SK_{ix}$, used for communicating with the medical server, when the timestamp $T_{11}$ and the validation parameters are legal; and the smart card and the user device of the patient, the medical server and the device of the doctor successfully negotiate the session keys with each other when verification of the session key $SK_{it}$ and the session key $SK_{ix}$, is successful;

S6.9: after the patient and the doctor communicate with each other by using the session key $SK_{it}$, the doctor performs a diagnosis $Dia_n$ on the patient, generates a current timestamp $T_{14}$, calculates verification parameters, and sends a message $MES_5^j$ to the medical server;

S6.10: after receiving the message $MES_5^x$, the medical server verifies legality of the timestamp $T_{14}$ and the validation parameters in the message $MES_5^x$; the bidirectional authentication is terminated when the timestamp $T_{14}$ and the validation parameters are not legal, or a source of a diagnostic result is reliable and verification of the medical server is successful when the timestamp $T_{14}$ and the validation parameters are legal;

S6.11: after the medical server verifies legality of the diagnostic result, the medical server generates a current timestamp $T_{15}$ and the electronic medical record of the patient, calculates validation parameters, and uploads the electronic medical record to the blockchain, and sends a message $MES_6^x$, to the user device of the patient; and S6.12: after receiving the message $MES_6^x$, the user device of the patient verifies legality of the timestamp $T_{15}$ and the validation parameters in the message $MES_6^x$; the bidirectional authentication is terminated when the timestamp $T_{15}$ and the validation parameters are not legal, or the electronic medical record is reliable and contents of the electronic medical record is held accountable when the timestamp $T_{15}$ and the validation parameters are legal.

In an embodiment, a method for verifying timestamps is $|T_n'-T_n| \leq \Delta T$, where $T_n$ is a timestamp contained in the message sent in any one of previous steps, $T_n'$, is a current timestamp obtained by the device when receiving the message, $\Delta T$ is a preset threshold time allowed in a communication process, an authentication process is terminated when a time difference exceeds the threshold time or a next step is proceeded when the time difference is less than the threshold time.

In an embodiment, the authentication parameters and the session keys are encrypted and calculated using an $E(GF_q)$ function of an elliptic curve selected by the medical server; the session keys $SK_{in}$, $SK_{nj}$, $SK_{ij}$, $SK_{it}$, $SK_{tx}$ and $SK_{ix}$ are generated by random numbers based on a Diffie-Hellman hard problem of the elliptic curve, and the random numbers are generated independently by communication parties and are not transmitted publicly.

In an embodiment, the message $MES_1^j$, the message $MES_2^j$, the message $MES_3^j$, the message $MES_4^j$, the message $MES_5^j$, the message $MES_6^j$, the message $MES_1^x$, the message $MES_2^x$, the message $MES_3^x$, the message $MES_4^x$ the message $MES_5^x$ and the message $MES_6^x$ are all transmitted within a common channel.

Compared with the related art, beneficial effects of the disclosure are as follows.

A use of the blockchain technology and a dynamic anonymous policy based on a symmetric encryption to protect privacy of the patients has achieved secure and reliable inter-hospital identity authentication of patients and inter-hospital access controls of electronic medical records of patients. The data of the patient cannot be tampered with, the true identity of the patient cannot be stolen, and contents of the medical record cannot be decrypted without the authorization of the patient.

The DHKC and the elliptic curve cryptography are used to encrypt and protect the key parameters in the authentication processes. Meanwhile, the three factor authentication method is added to encrypt the session key through independently generated parameters. The disclosure can resist various attacks, including the offline password guessing attacks, the session key disclosure attacks, and insider attacks, and ensure the security of authentication in the medical scenes and electronic medical record access controls.

BRIEF DESCRIPTION OF DRAWINGS

Accompanying drawings generally illustrate various embodiments by way of example rather than limitation, and are used together with the specification and claims to illustrate the embodiments of the disclosure. When appropriate, the same reference numerals are used throughout the drawings to refer to same or similar parts. Such the embodiments are illustrative and not intended as exhaustive or exclusive embodiments of the device or the method.

DETAILED DESCRIPTION OF EMBODIMENTS

Figure 1:
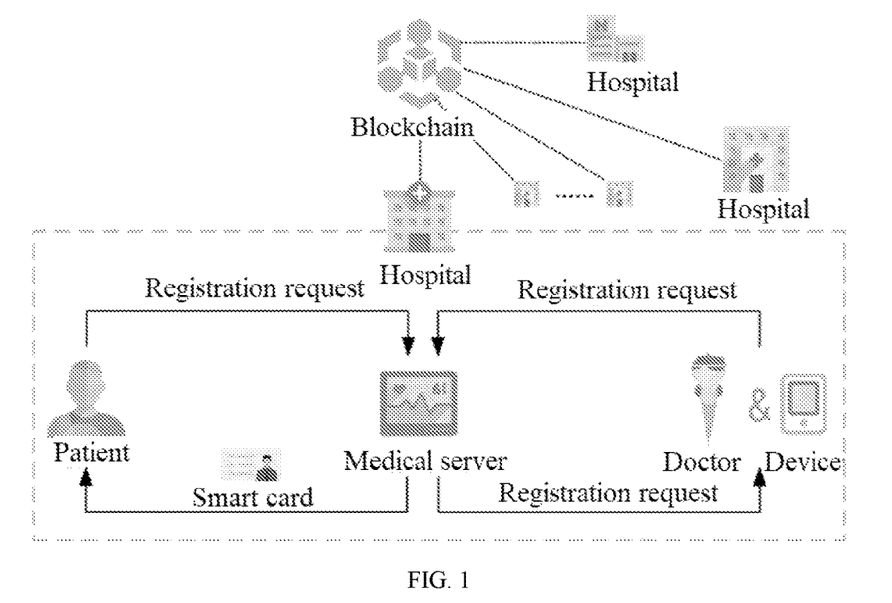
FIG. 1 is a schematic diagram of a relationship among a patient, a medical server, a doctor, and a blockchain in a system.

As shown in FIG. 1, the disclosure provides an inter-hospital electronic medical record access authentication protocol based on a blockchain, mainly including a patient, a medical server, and a doctor. A smart card of the patient and a device of the doctor can store messages. The patient and the doctor first register in the medical server, which stores registration messages of the patient and the doctor in the smart card of the patient and the device of the doctor, respectively. Multiple hospitals jointly maintain the blockchain and use the blockchain to achieve inter-hospital authentication and access controls of electronic medical records for patients.

Figure 2:
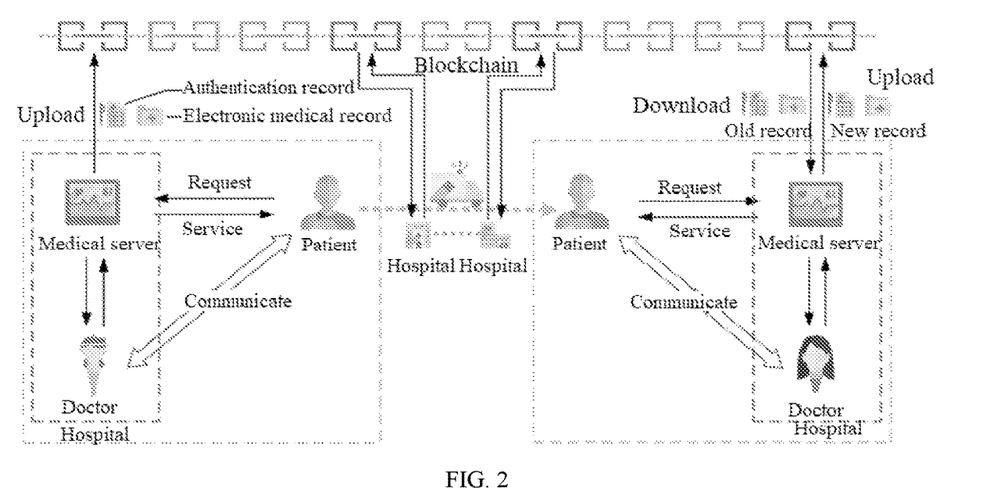
FIG. 2 is a schematic flowchart of an inter-hospital electronic medical record access authentication protocol based on a blockchain of the disclosure.

As shown in FIG. 2, a system of the inter-hospital electronic medical record access authentication protocol based on the a blockchain designed by the disclosure mainly includes three parties: the patient, the medical server, and the doctor; and the process is as follows:

The patient first requests initialization authentication and a diagnosis from a registered hospital to a medical server. After verifying a legal identity of the patient, the medical server sends message to a target doctor, and the three parties (i.e., the patient, the medical server and the target doctor) authenticate each other and negotiate session keys. After a communication between the doctor and the patient, a diagnostic report is generated and sent to the medical server. The medical server uploads an authentication record of the patient and an electronic medical record generated based on the diagnostic report to the blockchain, and sends the electronic medical record to the patient.

When the patient is transferred to another hospital, the patient submits requests of transfer authentication and a diagnostic to the medical server, and the medical server retrieves the patient authentication record on the blockchain based on the requests of the patient and verifies the legal identity of the patient. After the verification, the previous electronic medical record of the patient is decrypted based on the authorization of the electronic medical record of the patient, and the request of the diagnostic and previous medical record are sent to a target doctor. The patient, the medical server, and the doctor authenticate and negotiate the session key with each other. After the communication between the doctor and the patient, a diagnostic report is generated and sent to the medical server. The medical server uploads an authentication record of the patient and an electronic medical record generated based on the diagnostic report to the blockchain, and sends the electronic medical record to the patient.

Figure 3A:
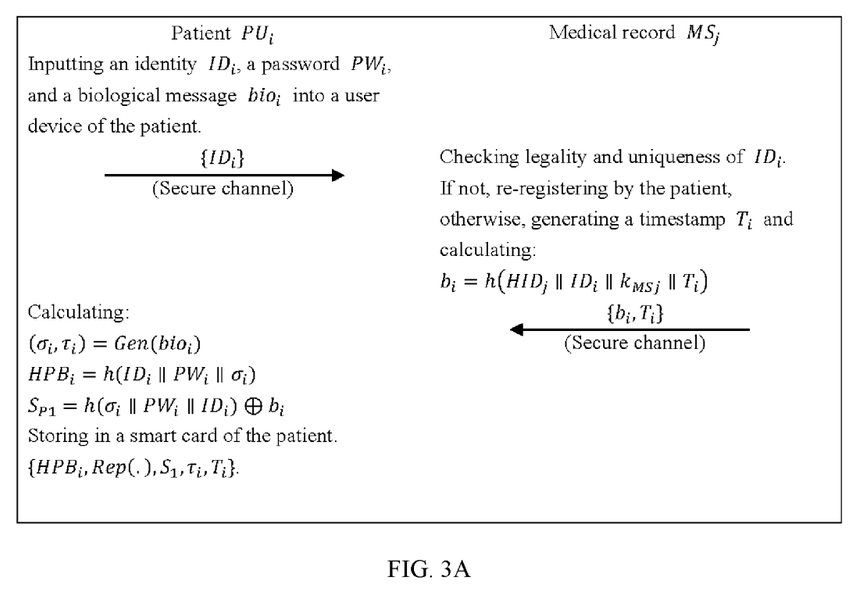
FIG. 3A is a schematic diagram of registering the patient on the medical server.
Figure 3B:
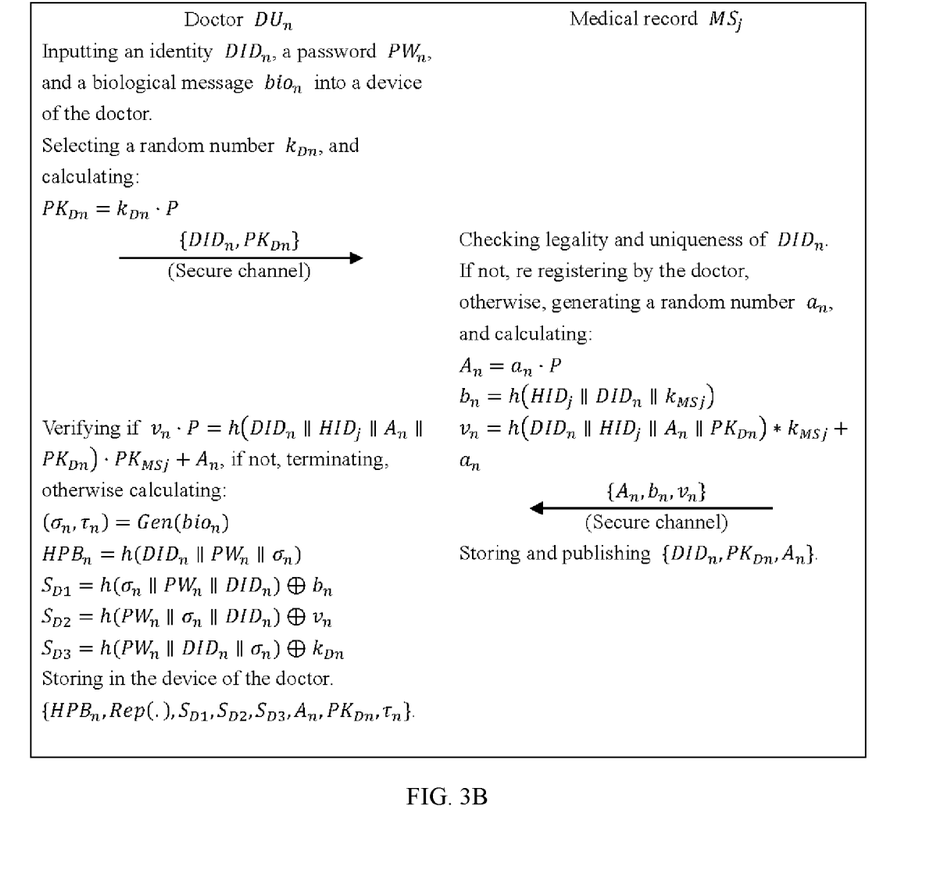
FIG. 3B is a schematic diagram of registering the doctor on the medical server.

As shown in FIG. 3, in the inter-hospital electronic medical record access authentication protocol based on a blockchain, a process of a patient and a doctor registering on a medical server includes the following steps.

S1: initializing the medical server: the medical server selects an $E(GF_q)$ function of an elliptic curve and selects a base point P on the elliptic curve; then selects a server key $k_{MSj}$ secretly stored in the medical server, and calculates the public key $PK_{MSj}$ through the $E(GF_q)$ function of the elliptic curve, finally exposes parameters $\{E(GF_q), P, PK_{MSj}\}$.

S2: a patient and a doctor submit registration requests to the medical server through a user device of the patient and a device of the doctor, after the medical server verifies legality of identities of the patient and the doctor, registration messages are fed back to the user device of the patient and the device of doctor, and the registration messages of the patient and the doctor are stored on a smart card of the patient and the device of the doctor respectively.

Steps of the S2 are as follows:

S2.1: the patient inputs an identity $ID_i$, a password $PW_i$ and a biological message $bio_i$ into the user device, and the user device sends the identity $ID_i$ to the medical server;

S2.2: after receiving and verifying legality of the identity $ID_i$ of the patient, the medical server calculates a secret value $b_i = h(HID_j\|ID_i\|k_{MSj}\|T_i)$ between the user device and the medical server, and sends the secret value to the user device, then the user device calculates a biological key $(\sigma_i, \tau_i) = Gen(bio_i)$, logs in to verify the parameter $HPB_i = h(ID_i\|PW_i\|\sigma_i)$, calculates $S_{p1} = h(\sigma_i\|PW_i\|ID_i) \oplus b_i$ for encrypting and storing $b_i$, and finally stores the registration message of the patient $\{HPB_i, Rep(\bullet)S_1, \tau_i T_i\}$ on the smart card;

S2.3: the doctor inputs an identity $DID_n$, a password $PW_n$, and a biological message $bio_n$ into the device of the doctor, and the device of the doctor sends the identity $DID_n$ to the medical server through a secure channel; and S2.4: after receiving and verifying legality of the identity $DID_n$ of the doctor, the medical server generates a random number $a_n$, calculates a public parameter $A_n = a_n \cdot P$, a secret value $b_n = h(HID_j\|DID_n\|k_{MSj})$, and an authentication parameter of the doctor $v\, n_n = h(DID_n\|HID_j\|A_n\|PK_{Dn})*k_{MSj} + a_n$ based on an elliptic curve point multiplication, and sends a registration message $\{A_n, b_n, a_n\}$ to the device of the doctor through a secure channel. The device of the doctor verifies the registration message returned by the medical server, and encrypts the registration message based on a biological key calculation $S_{D1} = h(\sigma_n\|PW_n\|DID_n) \oplus b_n$, $S_{D2} = h(PW_n\|n\|DID_n) \oplus v_n$, and $S_{D3} = h(PW_n\|DID_n\|\oplus_n) \oplus k_{Dn}$. Meanwhile, a login verification parameter $HPB_n = h(DID_n\|PW_n\|\sigma_n)$ is calculated, and $\{HPB_n, Rep(\bullet), S_{D1}, S_{D2}, S_{D3}, A_n, PK_{Dn}, \tau_n\}$ is stored on the device of the doctor.

Figure 4:
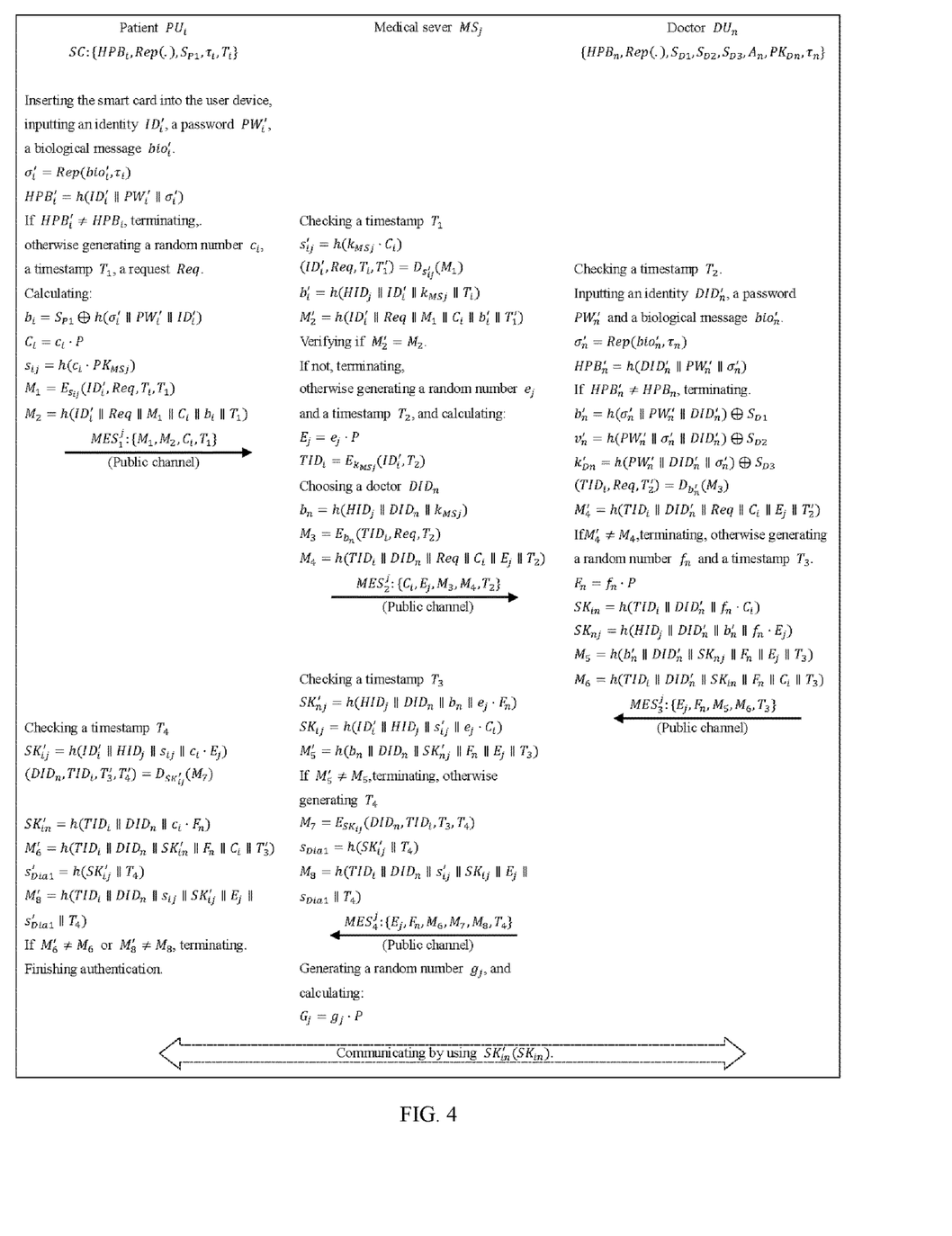
FIG. 4 is a schematic diagram of initialization authentication and key verification among the patient, the medical server, and the doctor.

As shown in FIG. 4, in the inter-hospital electronic medical record access authentication method based on a blockchain, the initialization authentication and a key verification process among the patient, the medical server, and the doctor includes following steps.

S4.1: The patient inserts the smart card into the user device, and inputs an identity $ID_i'$, a password $PW_i'$, a biological message $bio_i'$, and the user device calculates a biological key $\sigma_i'=Rep(bio_i'\tau_i)$, and logins a verification parameter $HPB_i'=h(ID_i'\|PW_i'\|\sigma_i')$, when $HPB_i'$ and $HPB_i$ stored in smart cards are not equal, a login is failed; when $HPB_i'$ is equal to $HPB_i$, the login is successful.

After the patient successfully logs in, the user device of the patient generates a random number $c_i$, a current timestamp $T_1$ and a diagnostic request Req, calculates $C_i=c_i\cdot P$ through the $E(GF_q)$ function of the elliptic curve, and recovers a secret values $b_i=S_{p1}\oplus h(\sigma_i'\|PW_i'\|ID_i')$ between the medical server and the patient from the registration message, and calculates $s_{ij}=h(c_i\cdot PK_{MSj})$ to encrypt authentication contents. An encrypted message is $M_1=E_{s_{ij}}(ID_i', Req, T_i, T_1)$, a verification parameter is $M_2-h(ID_i'\|Req\|M_1\|C_i\|b_i T_1)$. Finally, the user device sends a message $MES_1^j:\{M_1,M_2,C_i,T_1\}$ to the medical server.

S4.2: after receiving the message $MES_1^j$, the medical server generates a current timestamp $T_1'$, makes a judgment based on $|T_1'-T_1|\leq\Delta T$. When $|T_1'-T_1|\leq\Delta T$ is not established, the medical server terminates the authentication process; and when $|T_1'-T_1|\leq\Delta T$ is true, the medical server calculates a key $s_{ij}'=h(k_{MSj}\cdot C_i)$, and recovers $(ID_i', Req, T_i, T_1')=D_{s_{ij}}'(MO(M_1)$ from $M_1$, calculates $b_i':=h(HID_j\|ID_i'\|k_{MSj}\|T_i)$ and a comparative verification message $M_2'=h(ID_i'\|Req\|M_1\|C_i\|b_i'\|T_1')$; the initialization authentication is terminated, when $M_2'$ is not equal to $M_2$ in the message $MES_1$; or authentication from the smart card of the patient to the medical server is successful, when $M_2'$ is not equal to $M_2$ in the message $MES_1$.

S4.3: after authentication from the smart card of the patient to the medical server is successful, the medical server generates a random number $e_j$ and a current timestamp $T_2$, and calculates $E_j=e_j\cdot P$, temporary identity of the patient $TID_i=E_{k_{MSj}}(ID_i',T_2)$. The medical server selects doctors $DID_n$, calculates a shared secret value $b_n=h(HID_j\|DID_n\|k_{MSj})$ with the doctor, encrypts a transmission content $M_3=E_{b_n}(TID_i, Req, T_2)$, calculates a validation parameter $M_4=h(TID_i\|DID_n\|Req\|C_i\|E_j\|T_2)$, and sends a message $MES_2^j:\{C_i,E_j,M_3,M_4,T_2\}$ to the device of the doctor.

S4.4: the device of the doctor receives the message $MES_2^j$, decrypts $M_3: (TID_i, Req, T_2')=D_{b_n}'(M_3)$, verifies legality of a timestamp $T_2'$ and a validation parameter $M_4'=h(TID_i\|DID_n'\|Req\|C_i\|E_j\|T_2')$ in the message $MES_2^j$, the initialization authentication is terminated, when the timestamp $T_2'$ and the validation parameter $M_4'$ are not legal; or authentication from the medical server to the device of the doctor is successful, when the timestamp $T_2'$ and the validation parameter $M_4'$ are legal.

S4.5: after authentication from the medical server to the device of the doctor is successful, the device of the doctor generates a current timestamp $T_3$, a random number $f_n$, calculates $F_n=f_n\cdot P$, a session key $SK_{nj}=h(HID_j\|DID_n'\|b_n\|b_n'\|f_n\cdot E_j)$ for communicating with the medical server and a session key $SK_{in}=h(TID_i\|DID_n'\|f_n\cdot C_i)$ used for communicating with the patient, calculates validation parameters $M_5=h(b_n-'\|DID_n'\|SK_{nj}\|F_n\|E_j\|T_3)$ and $M_6=h(TID_i-\|DID_n'\|SK_{in}\|F_n\|C_i\|T_3)$, and sends a message $MES_3^j:\{E_j,F_n,M_5,M_6,T_3\}$ to the medical server.

S4.6: after receiving the message $MES_3^j$, the medical server verifies legality of the timestamp $T_3$ and the validation parameters in the message $MES_3^j$, the initialization authentication is terminated, when the timestamp $T_3$ and the validation parameters are not legal; or authentication from the device of the doctor to the medical server is successful, when the timestamp $T_3$ and the validation parameters are legal.

S4.7: after from the device of the doctor to the medical server is successful, the medical server generates a current timestamp $T_4$, a session key $SK_{nj}'=h(HID_j\|DID_n\|b_n\|e_j\cdot F_n)$ used for communicating with the doctor and a session key $SK_{ij}=h(ID_i'\|HID_j\|s_{ij}\|e_j\cdot C_i)$ used for communicating with the patient, calculates a verification parameter $M_5'=h(b_n\|DID_n\|SK_{nj}'\|F_n\|E_j\|T_3)$, the initialization authentication is terminated, when $M_5'$ is not equal to $M_5$; or the medical server calculates encrypted a message $M_7=E_{SK_{ij}}(DID_n,TID_i, T_3, T_4)$, authorization key $s_{Dia1}=h(SK_{ij}'\|T_4)$ and a verification parameter $M_8=h(TID_i\|DID_n\|s_{ij}'\|SK_{ij}\|E_j\|s_{Dia1}\|T_4)$, when $M_5'$ is equal to $M_5$; and sends a message $MES_4^j:\{E_j,F_n,M_6,M_7,M_8,T_4\}$ to the user device of the patient, then the medical server generates random numbers $g_j$, and calculates $G_j=g_j\cdot P$.

S4.8: after receiving the message $MES_4^j$, the user device of the patient verifies legality of the timestamp $T_4$ and the validation parameters in the message $MES_4^j$; the initialization authentication is terminated, when the timestamp $T_4$ and the validation parameters are not legal; or the user device calculates a the session key $SK_{ij}'=h(TID_i\|DID_n\|c_i\cdot F_n)$ used for communicating with the medical server, decrypts $M_7$ to obtain $(DID_n,TID_i,T_3',T_4')=D_{SK_{ij}}'(M_7)$ and calculates a session key $SK_{in}'=h(ID_i'\|HID_j\|s_{ij}\|c_i\cdot E_j)$ used for communicating with the doctor, a verification parameter $M_6'=h(TID_i-\|DID_n\|SK_{in}'\|F_n\|C_i\|T_3')$, authorization key $s_{Dia1}'=h(Sk_{ij}'\|T_4)$, a verification parameter $M_8'=h(TID_i\|DID_n\|s_{ij}\|SK_{ij}'\|E_j\|s_{Dia1}\|T_4)$, when the timestamp $T_4$ and the validation parameters are legal. When $M_6'$ and $M_8'$ pass the verification, the patient, the medical server, and the doctor successfully negotiate the session key with each other.

Figure 5:
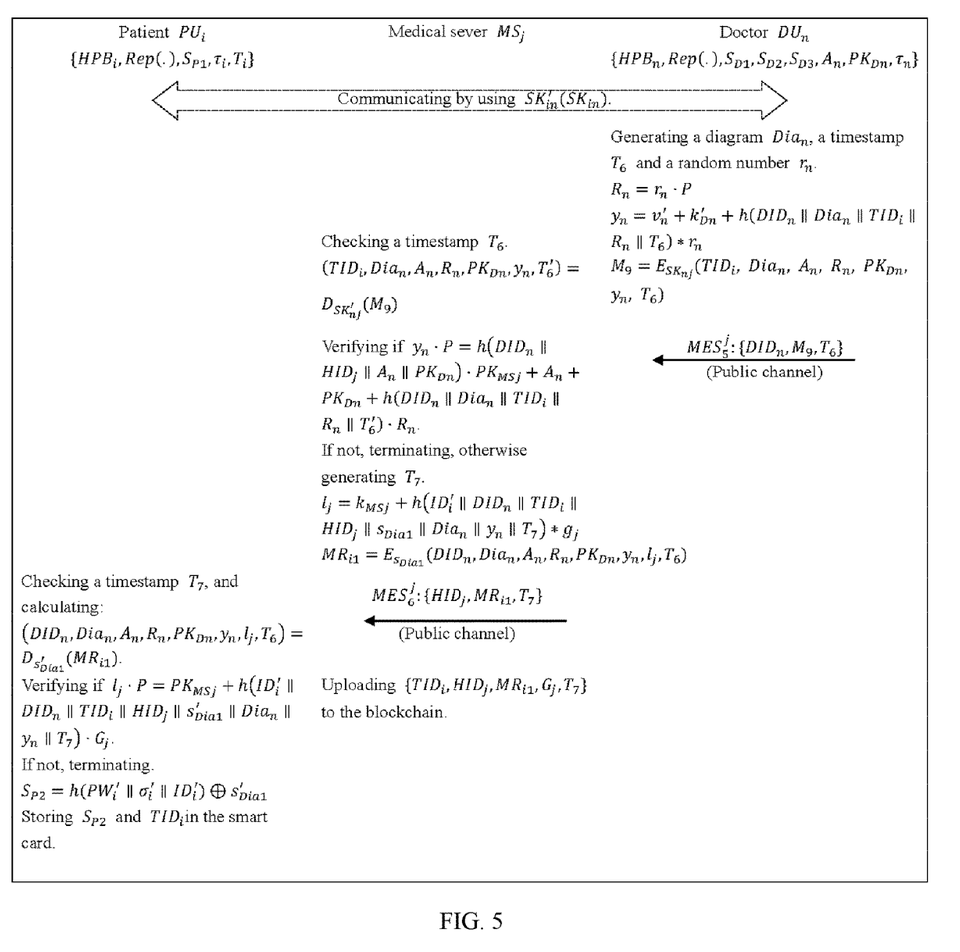
FIG. 5 is a schematic diagram of generating and uploading an electronic medical record by the medical server after initiate authentication of the patient and a diagnosis made by the doctor.

As shown in FIG. 5, after the patient initiates the authentication and the doctor makes the diagnosis, the medical server generates and uploads the electronic medical record, steps are as follows.

S4.9: after the patient and the doctor communicate using the session key $SK_{in}$, the doctor performs a diagnosis $Dia_n$ on the patient, generates a current timestamp $T_6$, and a random number $r_n$, and calculates $R_n=r_n\cdot P$, a verification parameter $y_n=v_n'+k'+h(DID_n\|Dia_n-\|TID_i\|R_n\|T_6)*r_n$, an encrypted message $M_9=E_{SK_{nj}}(TID_i,Dia_n,A_n,R_n,PK_{Dn}, y_n, T_6)$, and sends a message $MES_5^j:\{DID_n,M_9,T_6\}$ to the medical server.

S4.10: after receiving the message $MES_5^j$, the medical server verifies legality of the timestamp $T_6$ and the validation parameters in the message $MES_5^j$, the initialization authentication is terminated, when the timestamp $T_6$ and the validation parameters are not legal; or the medical server decrypts $(TID_i,Dia_n,A_n,R_n,PK_{Dn},y_n, T_6')=D_{SK_{nj}}'(M_9)$, when the timestamp $T_6$ and the validation parameters are legal, and then verifies whether $y_n\cdot P$ is equal to $h(DID_n\|HID_j\|A_n\|PK_{Dn})\cdot PK_{MSj}+A_n+PK_{Dn}+h(DID_n\|Dia_n\|TID_i\|R_n\|T_6')\cdot R_n$, the initialization authentication is terminated, when $y_n\cdot P$ is not equal to $h(DID_n\|HID_j\|A_n\|PK_{Dn})\cdot PK_{MSj}+A_n+PK_{Dn}+h(DID_n-\|Dia_n\|TID_i\|R_n\|T_6')\cdot R_n$, or a source of a diagnostic result is reliable, when $y_n \cdot P$ is not equal to $h(DID_n \| HID_j \| A_n \| PK_{Dn}) \cdot PK_{MSj} + A_n + PK_{Dn} \cdot h(DID_n \| Dia_n \| TID_i \| R_n \| T_6') \cdot R_n$.

S4.11: after the medical server verifies legality of the diagnosis result, the medical server generates a current timestamp $T_7$ and the electronic medical record of the patient, calculates a validation parameter $l_j = k_{MSj} + h(ID_i' \| DID_n \| TID_i \| HID_j \| s_{Dia1} \| Dia_n \| y_n \| T_7) * g_j$ and an encrypted message $MR_{i1} = E_{S_{Djal}}(DID_n, Dia_n, A_n, R_n, PK_{Dn}, y_n, l_j, T_6)$, uploads the electronic medical record $\{TID_i, HID_j, MR_{i1}, G_j, T_7\}$ to the blockchain, and sends a message $MES_6^j : \{HID_j, MR_{i1}, T_7\}$ to the user device of the patient.

S4.12: after receiving the message $MES_6^j$, the user device of the patient verifies legality of the timestamp $T_7$ and the validation parameters in the message $MES_6^j$, the initialization authentication is terminated, when the timestamp $T_7$ and the validation parameters are not legal; or the user device of the patient decrypts $(DID_n, Dia_n, A_n, R_n, PK_{Dn}, y_n, l_j, T_6) = D_{S_{Djal}}'(MR_{i1})$, when the timestamp $T_7$ and the validation parameters are legal, and the user device of the patient verifies whether $l_j \cdot P$ is equal to $PK_{MSj} + h(ID_i' \| DID_n \| TID_i \| HID_j \| s_{Dia1}' \| Dia_n \| y_n \| T_7) \cdot G_j$, the initialization authentication is terminated, when $l_j \cdot P$ is not equal to $PK_{MSj} + h(ID_i' \| DID_n \| TID_i \| HID_j \| s_{Dia1}' \| Dia_n \| y_n \| T_7) \cdot G_j$, the electronic medical record is reliable, contents of the electronic medical record is held accountable, when $l_j \cdot P$ is equal to $PK_{MSj} + h(ID_i' \| DID_n \| TID_i \| HID_j \| s_{Dia1}' \| Dia_n \| y_n \| T_7) \cdot G_j$, and the patient encrypts and saves an authorization key $S_{p2} = h(PW_i' \| \sigma_i' \| ID_i') \oplus s_{Dia1}'$ and a temporary identity $TID_i$.

Figure 6:
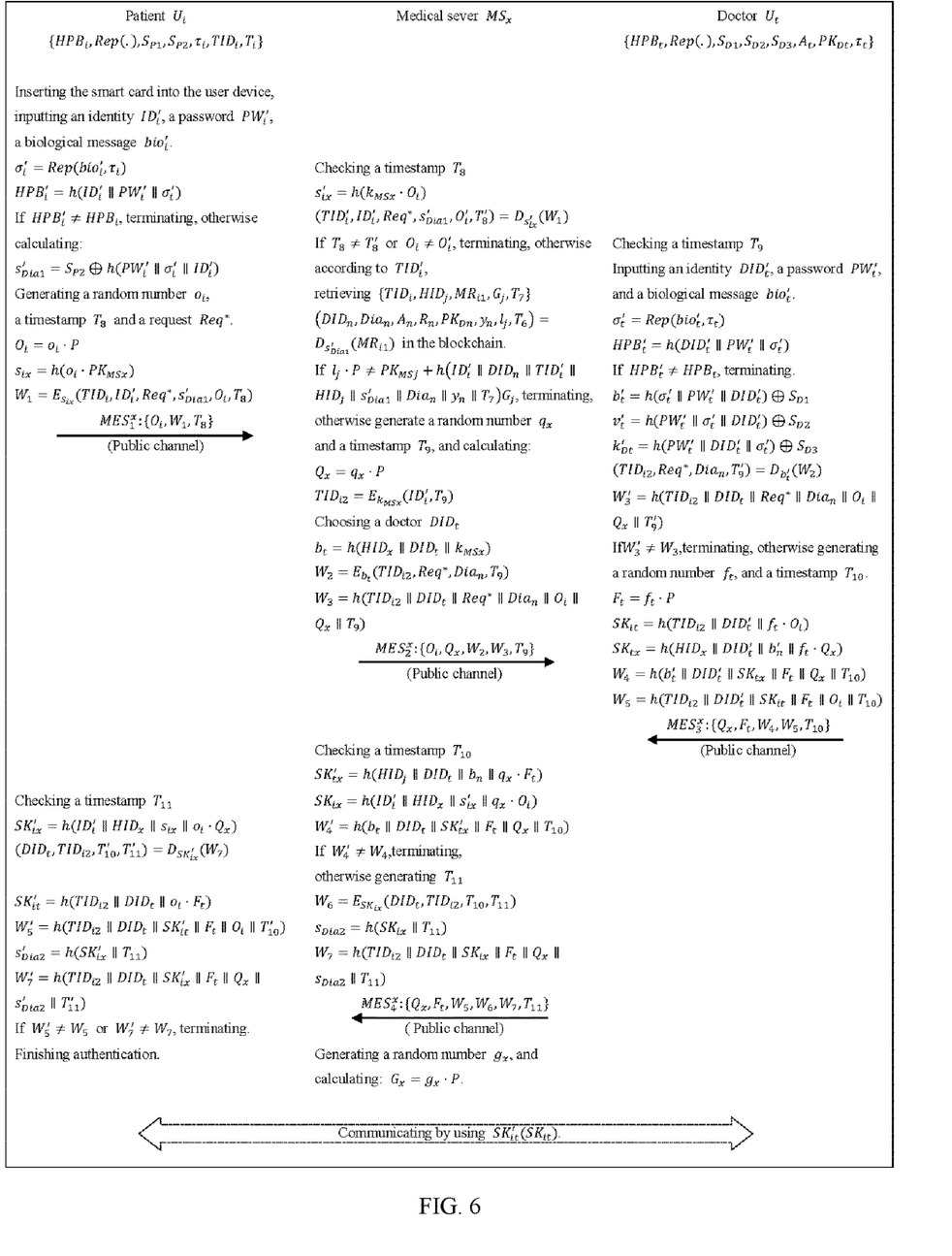
FIG. 6 is a schematic diagram of transfer authentication, key verification, and electronic medical record access control among the patient, the medical server, and the doctor after transferring the patient to another hospital.

As shown in FIG. 6, in the inter-hospital electronic medical record access authentication protocol based on a blockchain, processes of transfer authentication and key verification among the patient, a medical server and a doctor after the patient transferring to another hospital include the following steps.

S6.1: the patient inserts the smart card into the user device, inputs an identity $ID_i'$, a password $PW_i'$, and a biological message $bio_i'$ meanwhile, the user device calculates biological keys $\oplus_i' = Rep(bio_i', \tau_i)$ and logins a verification parameter $HPB_i' = h(ID_i' \| PW_i' \| \sigma_i')$, when $HPB_i'$ is not equal to the $HPB_i$ stored in the smart card, a login is failed; when $HPB_i'$ is equal to the $HPB_i$ stored in the smart card, the login is successful.

After the patient successfully logs in, the user device of the patient calculates an authorization key $s_{Dia1}' = S_{p2} \oplus h(PW_i' \| \sigma_i' \| ID_i')$, generates a random number $0_i$, a current timestamp $T_1$ and a diagnostic request Req, calculates $O_i = o_i \cdot P$ through the $E(GF_q)$ function of the elliptic curve, and calculates $s_{ix} = h(o_i \cdot PK_{MSx})$ to encrypt authentication contents, an encrypted message is $W_1 = E_{s_{ix}}(TID_i, ID_i', Req^*, s_{Dia1}' O_i, T_8)$, and finally sends a message $MES_1^x : \{O_i, W_1, T_8\}$ to the medical server.

S6.2: after receiving the message $MES_1^x$, the medical server verifies whether a timestamp is valid, and the transfer authentication is terminated, when the timestamp is not valid; or the medical server calculates a key $s_{ix}' = h(k_{MSx} \cdot O_i)$, recovers $(TID_i', ID_i', Req^*, s_{Dia1}' O_i', T_8') = D_{s_{ix}}'(W_1)$, when the timestamp is valid; the transfer authentication is terminated, when $O_i'$ is not equal to $T_8'$ are; or authentication from the smart card of the patient to the medical server is successful, when $O_i'$ is equal to $T_8'$.

S6.3: after the authentication from the smart card of the patient to the medical server is successful, the medical server retrieves and decrypts an electronic medical record $(DID_n, Dia_n, A_n, R_n, K_{Dn}, y_n, l_j, T_6) = D_{S_{Djal}}'(MR_{i1})$ based on $TID_i'$, and verifies legality of contents of the electronic medical record by verifying whether $l_j \cdot P$ is equal to $PK_{MSj} + h(ID_i' \| DID_n \| TID_i' \| HID_j \| s_{Dia1}' \| Dia_n \| y_n \| T_7) \cdot G_j$, when $l_j \cdot P$ is equal to $PK_{MSj} + h(ID_i' \| DID_n \| TID_i' \| HID_j \| s_{Dia1}' \| Dia_n \| y_n \| T_7) \cdot G_j$, the medical server generates a random number $q_x$ and the current timestamp $T_9$, and calculates $Q_x = q_x \cdot P$, a temporary identity of the patient $TID_{i2} = E_{k_{MSx}}(ID_i', T_9)$. The medical server selects a doctor $DID_t$, calculates a common secret value $b_t = h(HID_x \| DID_t \| k_{MSx})$ with the doctor, encrypts transmission contents $W_2 = E_{b_t}(TID_{i2}, Reg^*, Dia_n, T_9)$, calculates a verification parameter $W_3 = h(TID_{i2} \| DID_t \| Req^* \| Dia_n \| O_i Q_x \| T_9)$ and sends a message $MES_2^x : \{O_i, Q_x, W_2, W_3, T_9\}$ to the device of the doctor.

S6.4: the device of the doctor receives the message $MES_2^x$, decrypts $W_2$ $(TID_{i2}, Reg^*, Dia_n, T_9') = D_{b_t}'(W_2)$, verifies legality of a validation parameters $W_3' = h(TID_{i2} \| DID_t \| Req^* \| Dia_n \| O_i \| Q_x \| T_9')$ in the message $MES_2^x$, the transfer authentication is terminated, when the validation parameters $W_3'$ is not legal; or authentication from the medical server to the device of the doctor is successful, when the validation parameters $W_3'$ is legal.

S6.5: after the authentication from the medical server to the device of the doctor is successful, the device of the doctor generates a current timestamp $T_{10}$, a random number $f_t$, calculates $F_t = f_t \cdot P$, a session key $SK_{tx} = h(HID_x \| DID_t' \| b_n' \| f_t \cdot Q_x)$ used for communicating with the medical server and a session key $SK_{it} = h(TID_{i2} \| DID_t' \| f_t \cdot O_i)$ used for communicating with the patient, calculates validation parameters $W_4 = h(b_t' \| DID_t' \| SK_{tx} \| F_t \| Q_x \| T_{10})$ and $W_5 = h(TID_{i2} \| DID_t' \| SK_{it} \| F_t \| O_i \| T_{10})$, and sends a message $MES_3^x : \{Q_x, F_t, W_4, W_5, T_{10}\}$ to the medical server.

S6.6: after receiving the message $MES_3^x$, the medical server verifies legality of the timestamp $T_{10}$ and the validation parameters in the message $MES_3^2$; the transfer authentication is terminated, when the timestamp $T_{10}$ and the validation parameters are not legal; or authentication from the device of the doctor to the medical server is successful, when the timestamp $T_{10}$ and the validation parameters are legal.

S6.7: after the authentication from the device of the doctor to the medical server is successful, the medical server generates a current timestamp $T_{11}$, a session key $SK_{tx}' = h(HID_j \| DID_t \| b_n \| q_x \cdot F_t)$ used for communicating with the doctor and a session key $SK_{ix} = h(ID_i' \| HID_x \| s_{ix}' \| q_x \cdot O_i)$ used for communicating with the patient, calculates verification parameters $W_4' = h(b_t' \| DID_t \| SK_{tx}' \| F_t \| Q_x \| T_{10})$; the transfer authentication is terminated, when $W_4'$ is not equal to $W_4$; otherwise the medical server calculates an encrypted message $W_6 = E_{SK_{ix}}(DID_t, TID_{i2}, T_{10}, T_{11})$, an authorization key $s_{Dia2} = h(SK_{ix} \| T_{11})$, and a validation parameter $W_7 = h(TID_{i2} \| DID_t \| SK_{ix} \| F_t \| Q_x \| s_{Dia2} \| T_{11})$, and sends a message $MES_4^j : \{Q_x, F_t, W_5, W_6, W_7, T_{11}\}$ to the user device of the patient, then the medical server generates a random number $g_x$ and calculates $G_x = g_x \cdot P$.

S6.8: after receiving the message $MES_4^x$, the user device of the patient verifies legality of the timestamp $T_{11}$ and the validation parameters in the message $MES_4^x$, the transfer authentication is terminated, when the timestamp $T_{11}$ and the validation parameters are not legal; or the user device of the patient calculates the session key $SK_{ix}'=h(ID_i'\|HID_x\|s_{ix}\|o_i\cdot Q_x)$ used for communicating with the medical server, decrypts $W_7$ to obtain $(DID_t, TID_{i2}, T_{10}', T_{11}')=D_{SK_{ix}'}(W_7)$, calculates a session key $SK_{it}'=h(TID_{i2}\|DID_t\|o_i\cdot F_t)$ used for communicating with the doctor, a verification parameter $K_5'=h(TID_{i2}\|DID_t\|SK_{it}'\|F_t\|O_i\|T_{10}')$, an authorization key $s_{Dia2}'=h(SK_{ix}'\|T_{11})$, a verification parameter $W_7'=h(TID_{i2}\|DID_t\|SK_{ix}'\|F_t\|Q_x\|s_{Dia2}'\|T_{11}')$, when the timestamp $T_{11}$ and the validation parameters are legal; when $W_5'$ and $W_7'$ pass the verification, the session key is successfully negotiated among the patient, the medical server, and the doctor.

Figure 7:
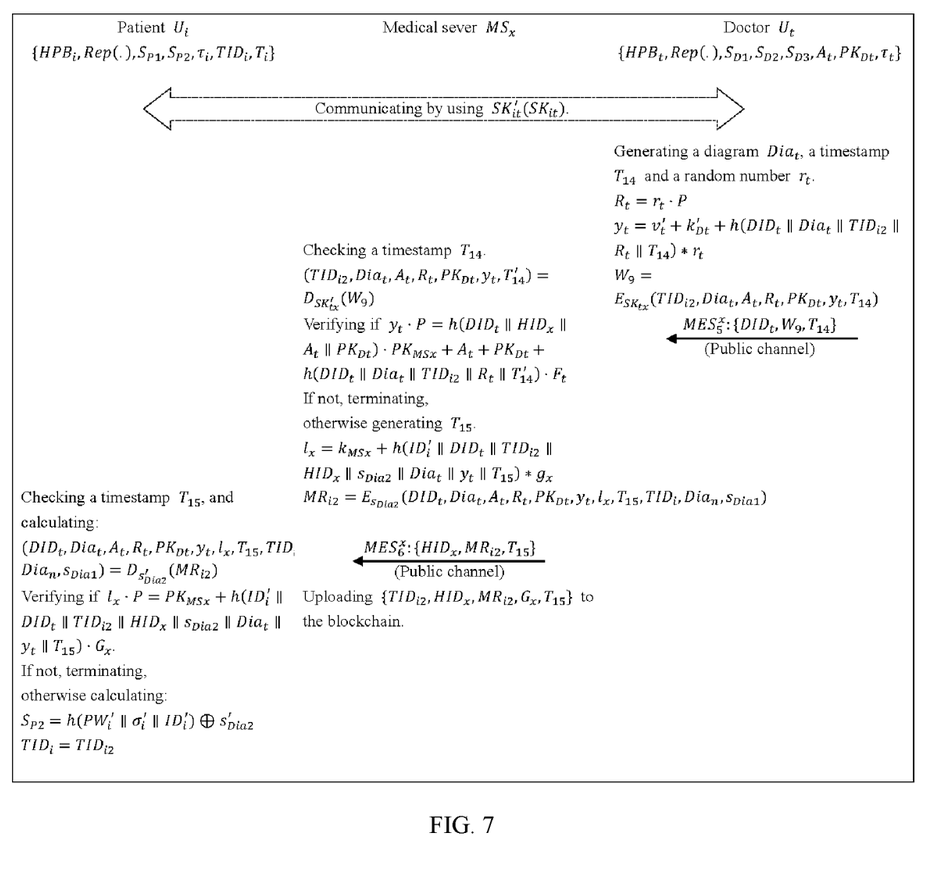
FIG. 7 is a schematic diagram of generating and uploading an electronic medical record by the medical server after the transfer authentication of the patient and a diagnosis made by the doctor.

As shown in FIG. 7, after the transfer authentication and a diagnosis made by the doctor, the medical server generates and uploads an electronic medical record including following steps.

S6.9: after the patient and doctor communicate using the negotiated session key $SK_{it}$, the doctor performs a diagnosis $Dia_t$ on the patient, generates a current timestamp $T_{14}$ and a random number $r_t$, calculates $R_t=r_t\cdot P$, a verification parameter $y_t=v_t'+k_{Dt}+h(DID_t\|Dia_t\|TID_{i2}\|R_t\|T_{14})*r_t$ and an encrypted message $W_9=E_{SK_{tx}}(TID_{i2}, Dia_t, A_t, R_t, PK_{Dt}, Y_t, T_{14})$, and sends a message $MES_5^x:\{DID_t, W_9, T_{14}\}$ to the medical server.

S6.10: after receiving the message $MES_5^x$, the medical server verifies legality of the timestamp $T_{14}$ and the validation parameters in the message $MES_5^x$; the transfer authentication is terminated, when the timestamp $T_{14}$ and the validation parameters are not legal; or the medical server decrypts $(TID_{i2}, Dia_t, A_t, R_t, PK_{Dt}, y_t, T_{14}'=D_{SK_{tx}'}(W_9))$, when the timestamp $T_{14}$ and the validation parameters are legal; and the medical server verifies whether $y_t\cdot P$ is equal to $h(DID_t\|HID_x\|A_t\|PK_{Dt})\cdot PK_{MSx}+A_t+PK\ Dt+h(DID_t\|Dia_t\|TID_{i2}\|R_t\|T_4')\cdot F_t$, the transfer authentication is terminated, when $y_t\cdot P$ is not equal to $h(DID_t\|HID_x\|A_t\|PK_{Dt})\cdot PK_{MSx}+A_t+PK_{Dt}+h(DID_t, Dia_t\|TID_{i2}\|R_t\|T_{14}')\cdot F_t$; or a source of a diagnostic result is reliable, when $y_t\cdot P$ is not equal to $h(DID_t\|HID_x\|A_t\|PK_{Dt})\cdot PK_{MSx}+A_t+PK_{Dt}+h(DID_t\|Dia_t\|TID_{i2}\|R_t\|T_{14}')\cdot F_t$.

S6.11: after the medical server verifies legality of the diagnostic result, the medical server generates a current timestamp $T_{15}$ and the electronic medical record of the patient, calculates a validation parameter $l_x=k_{MSx}+h(ID_i'\|DID_t\|TID_{i2}\|HID_x\|s_{Dia2}\|Dia_t\|Y_t\|T_{15})*g_x$ and an encrypted message $MR_{i2}E_{s_{Dia2}}(DID_t, Dia_t, A_t, R_t, PK_{Dt}, y_t, l_x, T_{15}, TID_i, Dia_n, s_{Dia1})$, uploads the electronic medical record $\{TID_{i2}, HID_x, MR_{i2}, G_x, T_{15}\}$ to the blockchain, and sends a message $MES_6^x:\{HID_x, MR_{i2}, T_{15}\}$ to the user device of the patient.

S6.12: after receiving the message $MES_6^x$, the user device of the patient verifies the legality of the timestamp $T_{15}$ and the validation parameters in the message $MES_6^x$; the transfer authentication is terminated, when the timestamp $T_{15}$ and the validation parameters are not legal; or the user device of the patient decrypts $(DID_t, Dia_t, A_t, R_t, PK_{Dt}, y_t, l_x, T_{15}, TID_i, Dia_n, s_{Dia1})=D_{s_{Dia2}'}(MR_{i2})$, when the timestamp $T_{15}$ and the validation parameters are legal; and the user device of the patient verifies whether $l_x\cdot P$ is equal to $PK_{MSx}+h(ID_i'\|DID_t\|TID_{i2}\|HID_x\|S_{Dia2}\|Dia_t\|y_t\|T_{15})\cdot G_x$; the transfer authentication is terminated, when $l_x\cdot P$ is not equal to $PK_{MSx}+h(ID_i'\|DID_t\|TID_{i2}\|HID_x\|s_{Dia2}\|Dia_t\|y_t\|T_{15})\cdot G_x$; or the electronic medical record is reliable and contents of the electronic medical record is held accountable, when $l_x\cdot P$ is equal to $PK_{MSx}h(ID_i'\|DID_t\|TID_{i2}\|HID_x\|s_{Dia2}\|Dia_t\|Y_t\|T_{15})\cdot G_x$; and then the patient encrypts and saves an authorization key $S_{p2}=h(PW_i'\|\sigma_i'\|ID_i')\oplus s_{Dia2}'$ and a temporary identity $TID_{i2}$.

The above-described embodiments are only a description of the illustrated method of the disclosure, not a limitation of the scope of the disclosure. Without departing from the spirit of the design of the disclosure, various modifications and changes made by those skilled in the art to the technical solution of the disclosure shall fall within the scope of protection determined by the claims of the disclosure.

What is claimed is:

1. An inter-hospital electronic medical record access authentication method based on a blockchain, comprising the following steps:
    s1: initializing a medical server;
    s2: submitting, by a user device of a patient and a device of a doctor, registration requests to the medical server; feeding, by the medical server, registration messages back to the user device of the patient and the device of the doctor after verifying legality of the patient and the doctor; and storing the registration messages of the patient and the doctor on a smart card of the patient and the device of the doctor respectively;
    s3: submitting, by the user device of the patient, an initialize authentication request to the medical server;
    s4: performing, by the doctor, a diagnosis on the patient after completing initialize authentication among the patient, the medical server and the doctor for negotiating session keys for communications; and uploading, by the medical server, an electronic medical record of the patient to the blockchain;
    s5: submitting, by the patient, a transfer authentication request to another medical server of another hospital where the patient is located when the patient is transferred to the another hospital; and
    s6: authorizing, by the patient, the another medical server to access the electronic medical record of the patient after completing transfer authentication among the patient, the another medical server, and another doctor in the another hospital for negotiating and verifying session keys for communications; performing, by the another doctor, a diagnosis on the patient; and uploading, by the another medical server, another electronic medical record of the patient to the blockchain;
    wherein the initializing a medical server in the s1 comprises: selecting, by the medical server, an $E(GF_q)$ function of an elliptic curve; selecting a base point P on the elliptic curve; then selecting a server key $k_{MSj}$ and storing the server key $k_{MSj}$ in the medical server; and calculating, by the medical server, a public key $PK_{MSj}$ through the E(GF) function of the elliptic curve, and exposing parameters $\{E(GF_q), P, PK_{MSj}\}$.

2. The inter-hospital electronic medical record access authentication method based on the blockchain as claimed in claim 1, wherein the s2 comprises:
    s2.1: inputting, by the patient, an identity $ID_i$, a password $PW_i$ and a biological message $bio_i$ into the user device of the patient; and sending, by the user device of the patient, the identity $ID_i$ to the medical server through a secure channel;
    s2.2: calculating, by the medical server, a secret value $b_i$ between the patient and the medical server after receiving and verifying legality of the identity $ID_i$ of the patient; and sending, by the medical server, the registration message of the patient to the user device of the patient through a secure channel for the storing;

s2.3: inputting, by the doctor, an identity $DID_n$, a password $PW_n$, and a biological message $bio_n$ into the device of the doctor, and sending, by the device of the doctor, the identity $DID_n$ to the medical server through a secure channel; and s2.4: calculating, by the medical server, a secret value $b_n$ between the doctor and the medical server after receiving and verifying legality of the identity $DID_n$ of the doctor; and sending, by the medical server, the registration message of the doctor to the device of the doctor through a secure channel for the storing.

3. The inter-hospital electronic medical record access authentication method based on the blockchain as claimed in claim 1, wherein the initialize authentication in the s4 is based on bidirectional authentication and key negotiation and verification among the smart card and the user device of the patient, the medical server and the device of the doctor; and uploading the electronic medical record of the patient in the s4 is based on a mutual confirmation among the smart card and the user device of the patient, the medical server and the device of the doctor, and the electronic medical record is uploaded to the blockchain by the medical server.

4. The inter-hospital electronic medical record access authentication method based on the blockchain as claimed in claim 3, wherein the s4 comprises:

s4.1: inserting, by the patient, the smart card into the user device; and generating, by the user device, a current timestamp $T_1$ through the registration message in the smart card after passing identity authentication; calculating, by the user device, verification parameters; and sending, by the user device, a message $MES_1^j$ to the medical server;

s4.2: verifying, by the medical server, legality of the timestamp $T_1$ and the validation parameters in the message $MES_1^j$ after receiving the message $MES_1^j$; wherein the bidirectional authentication is terminated when the timestamp $T_1$ and the validation parameters are not legal, or an authentication from the smart card of the patient to the medical server is successful when the timestamp $T_1$ and the validation parameters are legal;

s4.3: generating, by the medical server, a temporary identity $TID_i$ of the patient and a current timestamp $T_2$ after the authentication from the smart card of the patient to the medical server is successful; calculating, by the medical server, verification parameters; and sending, by the medical server, a message $MES_2^j$ to the device of the doctor;

s4.4: receiving, by the device of the doctor, the message $MES_2^j$ and verifying legality of the timestamp $T_2$ and the validation parameters in the message $MES_2^j$ wherein the bidirectional authentication is terminated when the timestamp $T_2$ and the validation parameters are not legal, or an authentication from the medical server to the device of the doctor is successful when the timestamp $T_2$ and the validation parameters are legal;

s4.5: generating, by the device of the doctor, a current timestamp $T_3$, a session key $SK_{nj}$ used for communicating with the medical server and a session key $SK_{in}$ used for communicating with the patient after the authentication from the medical server to the device of the doctor is successful; calculating, by the device of the doctor, validation parameters; and sending, by the device of the doctor, a message $MES_3^j$ to the medical server;

s4.6: verifying, by the medical server, legality of the timestamp $T_3$ and the validation parameters in the message $MES_3^j$ after receiving the message $MES_2^j$ wherein the bidirectional authentication is terminated when the timestamp $T_3$ and the validation parameters are not legal, or an authentication from the device of the doctor to the medical server is successful when the timestamp $T_3$ and the validation parameters are legal;

s4.7: generating, by the medical server, a current timestamp $T_4$, a session key $SK_{nj}'$ used for communicating with the doctor and a session key $SK_{ij}$ used for communicating with the patient after the authentication from the device of the doctor to the medical server is successful; calculating, by the medical server, validation parameters; and sending, by the medical server, a message $MES_4^j$ to the user device of the patient;

s4.8: verifying, by the user device, legality of the timestamp $T_4$ and the validation parameters in the message $MES_4^j$ after receiving the message $MES_4^j$ wherein the bidirectional authentication is terminated when the timestamp $T_4$ and the validation parameters are not legal, or the user device calculates and verifies a session key $SK_{in}'$ used for communicating with the doctor and a session key $SK_{ij}'$ used for communicating with the medical server when the timestamp $T_4$ and the validation parameters are legal; and the smart card and the user device of the patient, the medical server and the device of the doctor successfully negotiate the session keys with each other when the verification of the session key $SK_{in}'$ and the session key $SK_{ij}'$ is successful;

s4.9: performing, by the doctor, a diagnosis $Dia_n$ on the patient after the patient and the doctor communicating by using the session key $SK_{in}$; generating, by the device of the doctor, a current timestamp $T_6$; calculating, by the device of the doctor, verification parameters, and sending, by the device of the doctor, a message $MES_5^j$ to the medical server;

s4.10: verifying, by the medical server, legality of the timestamp $T_6$ and the validation parameters in the message $MES_5^j$ after receiving the message $MES_5^j$; wherein the bidirectional authentication is terminated when the timestamp $T_6$ and the validation parameters are not legal, or a source of a diagnostic result is reliable and verification of the medical server is successful when the timestamp $T_6$ and the validation parameters are legal;

s4.11: generating, by the medical server, a current timestamp $T_7$ and the electronic medical record of the patient after the medical server verifies legality of the diagnosis result; calculating, by the medical server, validation parameters; uploading, the medical server, the electronic medical record to the blockchain; and sending, by the medical server, a message $MES_6^j$ to the user device of the patient; and s4.12: verifying, by the user device of the patient, legality of the timestamp $T_7$ and the validation parameters in the message $MES_6^j$ after receiving the message $MES_6^j$; wherein the bidirectional authentication is terminated when the timestamp $T_7$ and the validation parameters are not legal, or the electronic medical record is reliable and contents of the electronic medical record is held accountable when the timestamp $T_7$ and the validation parameters are legal.

5. The inter-hospital electronic medical record access authentication method based on a blockchain as claimed in claim 4, wherein a method for verifying timestamps is $|T_n'-T_n| \le \Delta T$; $T_n$ is a timestamp contained in a message, $T_n'$ is a current timestamp obtained by a device when receiving the message, $\Delta T$ is a preset threshold time allowed in a communication process; an authentication process is terminated when a time difference exceeds the preset threshold time, or a next step is proceeded when the time difference is less than the preset threshold time.

6. The inter-hospital electronic medical record access authentication method based on a blockchain as claimed in claim 4, wherein the authentication parameters and the session keys are encrypted and calculated using the E(GF) function of the elliptic curve selected by the medical server; the session keys $SK_{in}$, $SK_{nj}$, and $SK_{ij}$ are generated by random numbers based on a Diffie-Hellman hard problem of the elliptic curve, and the random numbers are generated independently by communication parties and are not transmitted publicly.

7. The inter-hospital electronic medical record access authentication method based on a blockchain as claimed in claim 4, wherein the message $MES_1^j$, the message $MES_2^j$, the message $MES_3^j$, the message $MES_4^j$, the message $MES_5^j$, and the message $MES_6^j$ are all transmitted within a common channel.

8. The inter-hospital electronic medical record access authentication method based on a blockchain as claimed in claim 1, wherein the transfer authentication in the s6 is based on bidirectional authentication and key negotiation and verification among the smart card and the user device of the patient, the another medical server and a device of the another doctor; and uploading the another electronic medical record in the s6 is based on mutual confirmation among the smart card and the user device of the patient, the another medical server and the device of the another doctor, and the another electronic medical record is uploaded to the blockchain by the another medical server.

9. The inter-hospital electronic medical record access authentication method based on a blockchain as claimed in claim 8, wherein the s6 comprises:
  s6.1: inserting, by the patient, the smart card into the user device; and generating, by the user device, a current timestamp $T_8$ through the registration message in the smart card after passing identity authentication; calculating, by the user device, verification parameters; and sending, by the user device, a message $MES_1^x$ to the medical server;
  s6.2: verifying, by the medical server, legality of the timestamp $T_8$ and the validation parameters in the message $MES_1^x$ after receiving the message $MES_1^x$; wherein the bidirectional authentication is terminated when the timestamp $T_8$ and the validation parameters are not legal, or an authentication from the smart card of the patient to the medical server is successful when the timestamp $T_8$ and the validation parameters are legal;
  s6.3: generating, by the medical server, a temporary identity $TID_i$ of the patient after the authentication from the smart card of the patient to the medical server is successful; downloading, by the medical server, the electronic medical record of the patient from the blockchain based on authorization of the electronic medical record of the patient; generating, by the medical server, a current timestamp $T_9$; calculating, by the medical server, verification parameters; and sending, by the medical server, a message $MES_2^x$ to the device of the doctor;
  s6.4: receiving, by the device of the doctor, the message $MES_2^x$ and verifying legality of the timestamp $T_9$ and the validation parameters in the message $MES_2^x$; wherein the bidirectional authentication is terminated when the timestamp $T_9$ and the validation parameters are not legal, or an authentication from the medical server to the device of the doctor is successful when the timestamp $T_9$ and the validation parameters are legal;
  s6.5: generating, by the device of the doctor, a current timestamp $T_{10}$, a session key $SK_{tx}$ used for communicating with the medical server and a session key $SK_{it}$ used for communicating with the patient after the authentication from the medical server to the device of the doctor is successful; calculating, by the device of the doctor, validation parameters; and sending, by the device of the doctor, a message $MES_3^x$ to the medical server;
  s6.6: verifying, by the medical server, legality of the timestamp $T_{10}$ and the validation parameters in the message $MES_3^x$ after receiving the message $MES_3^x$; wherein the bidirectional authentication is terminated when the timestamp $T_{10}$ and the validation parameters are not legal, or an authentication from the device of the doctor to the medical server is successful when the timestamp $T_{10}$ and the validation parameters are legal;
  s6.7: generating, by the medical server, a current timestamp $T_{11}$, a session key $SK_{tx}'$ used for communicating with the doctor and a session key $SK_{ix}$ used for communicating with the patient after the authentication from the device of the doctor to the medical server is successful; calculating, by the medical server, validation parameters; and sending, by the medical server, a message $MES_4^x$ to the user device of the patient;
  s6.8: verifying, by the user device, legality of the timestamp $T_{11}$ and the validation parameters in the message $MES_4^x$ after receiving the message $MES_4^x$; wherein the bidirectional authentication is terminated when the timestamp $T_{11}$ and the validation parameters are not legal, or the user device calculates and verifies a session key $SK_{it}'$ used for communicating with the doctor and a session key $SK_{ix}'$ used for communicating with the medical server when the timestamp $T_{11}$ and the validation parameters are legal; and the smart card and the user device of the patient, the medical server and the device of the doctor successfully negotiate the session keys with each other when the verification of the session key $SK_{it}'$ and the session key $SK_{ix}'$ is successful;
  s6.9: performing, by the doctor, a diagnosis $Dia_t$ on the patient after the patient and the doctor communicating by using the session key $SK_{it}$; generating, by the device of the doctor, a current timestamp $T_{14}$; calculating, by the device of the doctor, verification parameters, and sending, by the device of the doctor, a message $MES_5^x$ to the medical server;
  s6.10: verifying, by the medical server, legality of the timestamp $T_{14}$ and the validation parameters in the message $MES_5^x$ after receiving the message $MES_5^x$; wherein the bidirectional authentication is terminated when the timestamp $T_{14}$ and the validation parameters are not legal, or a source of a diagnostic result is reliable and verification of the medical server is successful when the timestamp $T_{14}$ and the validation parameters are legal;

s6.11: generating, by the medical server, a current timestamp $T_{15}$ and the electronic medical record of the patient after the medical server verifies the legality of the diagnostic result; calculating, by the medical server, validation parameters; uploading, the medical server, the electronic medical record to the blockchain; and sending, by the medical server, a message $MES_6^x$ to the user device of the patient; and s6.12: verifying, by the user device of the patient, legality of the timestamp $T_{15}$ and the validation parameters in the message $MES_6^x$ after receiving the message $MES_6^x$; wherein the bidirectional authentication is terminated when the timestamp $T_{15}$ and the validation parameters are not legal, or the electronic medical record is reliable and contents of the electronic medical record is held accountable when the timestamp $T_{15}$ and the validation parameters are legal.

\* \* \* \* \*